(12) United States Patent
Adell

(10) Patent No.: US 9,378,660 B1
(45) Date of Patent: Jun. 28, 2016

(54) DENTAL ARCH MODELS

(71) Applicant: Loren S. Adell, Sunnyvale, TX (US)

(72) Inventor: Loren S. Adell, Sunnyvale, TX (US)

(73) Assignees: Loren S. Adell, Sunnyvale, TX (US); Michael Adell, Sunnyvale, TX (US)

( * ) Notice: Subject to any disclaimer, the term of this patent is extended or adjusted under 35 U.S.C. 154(b) by 331 days.

(21) Appl. No.: 13/775,774

(22) Filed: Feb. 25, 2013

(51) Int. Cl.
*G09B 23/24* (2006.01)
*A61C 11/00* (2006.01)
*G09B 23/28* (2006.01)

(52) U.S. Cl.
CPC .................................. *G09B 23/283* (2013.01)

(58) Field of Classification Search
CPC ........ G09B 23/28; G09B 23/32; G09B 23/34; G09B 23/283
See application file for complete search history.

(56) References Cited

U.S. PATENT DOCUMENTS

| | | | | |
|---|---|---|---|---|
| 2,085,054 A | * | 6/1937 | Trevisan | 220/835 |
| 4,798,916 A | * | 1/1989 | Engel et al. | 174/67 |
| 6,308,831 B1 | * | 10/2001 | Saxe et al. | 206/449 |
| 2005/0089815 A1 | * | 4/2005 | Lee | 433/60 |

OTHER PUBLICATIONS

"Paradigm Dental Demonstration Models," https://web.archive.org/web/20030908173641/http://www.paradigmmodels.com/products.html, Sep. 8, 2003.*

* cited by examiner

*Primary Examiner* — Sam Yao
*Assistant Examiner* — Jennifer Fassett
(74) *Attorney, Agent, or Firm* — George L. Boller

(57) ABSTRACT

An arch model has a set of teeth and a wall which bridges the set of teeth and has a surface opposite the set of teeth. A sheet containing indicia is placed between the surface of the arch model and a transparent zone of a cover. The cover is separably attached to the arch model. The resulting arch model has the sheet containing indicia disposed between the surface of the arch model and the transparent zone of the cover so that the indicia can be read through the cover. The sheet can be replaced by separating the cover from the arch model, replacing the sheet, and then re-attaching the cover.

16 Claims, 4 Drawing Sheets

DENTAL ARCH MODELS

TECHNICAL FIELD

This invention relates to dentistry. In particular the invention relates to dental arch models.

BACKGROUND

There are various types of dental arch models. One type is known as a typodont.

A typodont is a synthetic life-like model of ideal upper and lower dental arches which can be articulated between closed and open conditions. Typodonts are used for various purposes including teaching, demonstration, and/or advertisement of dental products such as orthodontic appliances.

A manufacturer of orthodontic appliances may advertise its products by mounting them on teeth of a typodont. For identifying a manufacturer, a typodont may contain information such as the manufacturer's name and/or logo. The information is typically placed to be seen when a person views a top surface of the typodont's upper dental arch. The information is made permanent by embedding it in the typodont at time of fabrication.

The fabrication process comprises placing a sheet containing printed information on a surface of one of the dental arch models, typically on a top surface of the upper arch model, and then overmolding at least the informational sheet with transparent material. Once the overmold material has set to a hardened condition, the sheet material becomes trapped in place and can be viewed through the transparent material.

Another type of dental arch model comprises a single arch, either an upper arch or a lower arch. The model may contain an ideal dental arch or it may be an irregular dental arch which can be used for educational purposes.

SUMMARY OF THE INVENTION

Because the commercial typodont which has just been described encapsulates the sheet of information inside the finished typodont, the sheet cannot be removed and replaced without damaging or destroying the typodont.

Briefly, this disclosure introduces a typodont fabricated by a method which allows a sheet of informational material to be embodied in a typodont in a protected manner without overmolding. The method provides a typodont from which an informational sheet can be conveniently removed and replaced without damaging the typodont. Because a typical typodont, even when mass-produced on a small scale, is not inexpensive, the method provides an economical way to re-use a typodont by allowing the informational material to be replaced without damaging the typodont.

The method comprises: fabricating an arch model having a set of teeth and a wall which bridges the set of teeth and has a surface opposite the set of teeth; placing a sheet containing printed matter between the surface of the arch model and a transparent zone of a cover; and separably attaching the cover to the arch model.

The resulting arch model comprises a set of teeth and a wall which bridges the set of teeth and has a surface opposite the set of teeth; a sheet containing printed matter is disposed between the surface of the arch model and a transparent zone of a cover which is separably attached to the arch model. The separable attachment allows the same cover to be detached and either reattached or replaced by a different cover of like size and shape.

The foregoing summary, accompanied by further detail of the disclosure, will be presented in the Detailed Description below with reference to the following drawings that are part of this disclosure.

DETAILED DESCRIPTION

Figure 1:
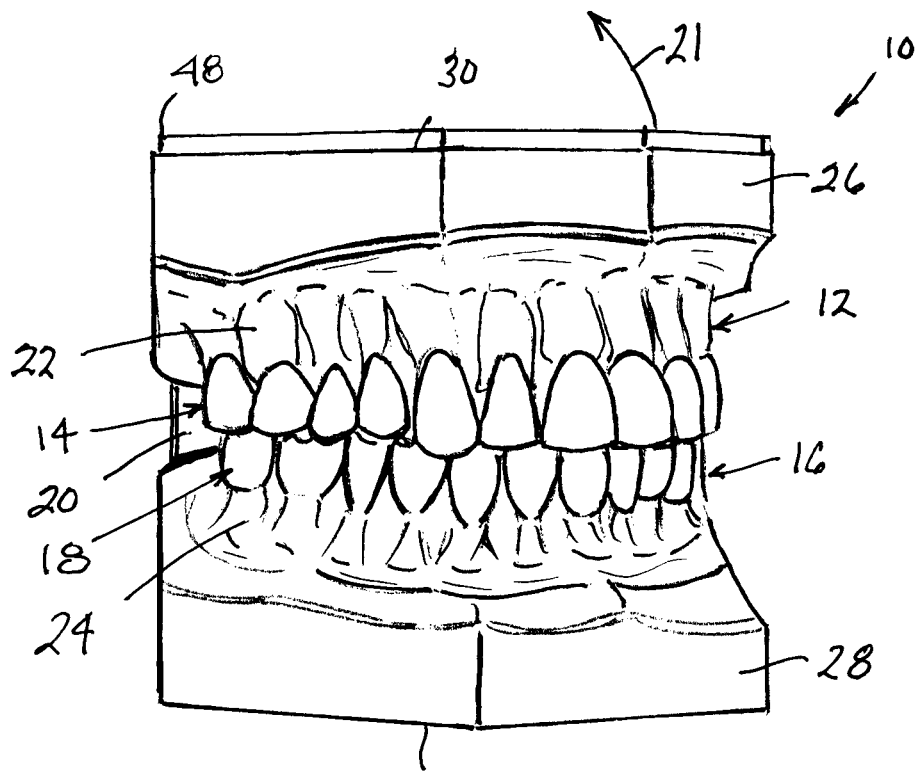
FIG. 1 is a perspective view of a typodont.
Figure 2:
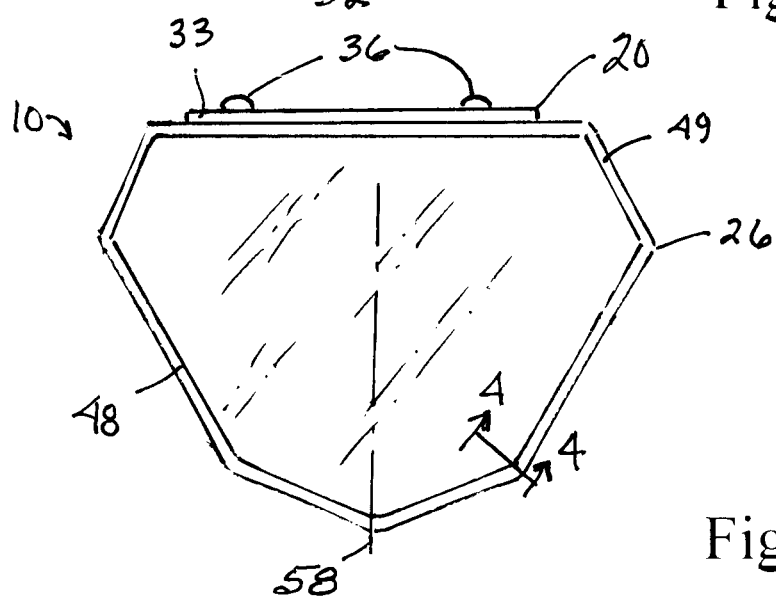
FIG. 2 is a top plan view of the typodont of FIG. 1.
Figure 3:
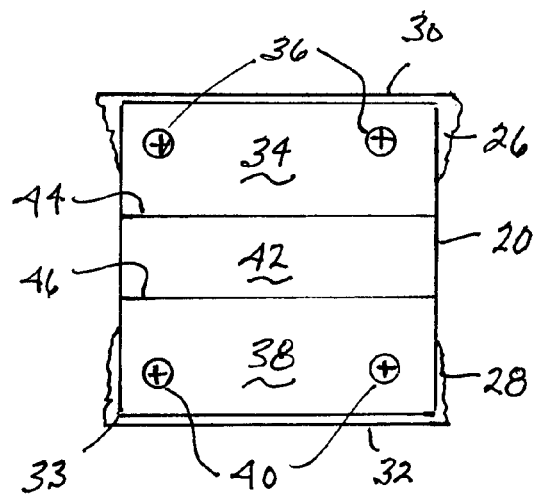
FIG. 3 is a rear view of the typodont of FIG. 1.
Figure 4:
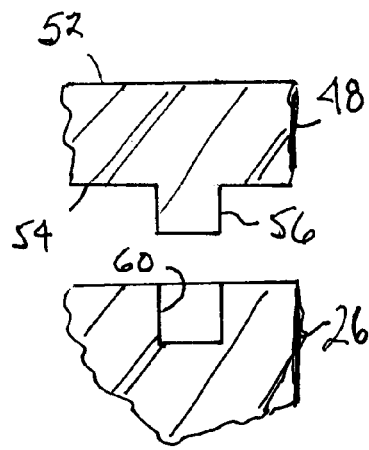
FIG. 4 is an enlarged cross section view in the direction of arrows 4-4 in FIG. 2.

FIGS. 1-7 show an embodiment of a typodont 10 comprising an upper arch model 12 having a set of upper teeth 14 and a lower arch model 16 having a set of lower teeth 18, and a connection 20 for articulating the arches between closed condition shown in FIG. 1 and open condition, suggested by arrow 21 representing swinging motion of upper arch model 12 away from lower arch model 16.

Each set of teeth 14, 18 is fixedly set in a model of the respective gum 22, 24. Each gum 22, 24 is bridged by a respective wall 26, 28 opposite the respective set of teeth 14, 18. Wall 26 has a flat top surface 30 opposite set of upper teeth 14 and a side surface extending around the perimeter of top surface 30. Wall 28 has a flat bottom surface 32 opposite set of lower teeth 18 and a side surface extending around the perimeter of bottom wall 32.

Hence typodont 10 is seen to comprise: a model of an oral cavity containing a model of an upper dental arch and a model of a lower dental arch. It further comprises a connection for articulating the arches between closed and open conditions.

The model of an upper dental arch contains a wall and a model of an upper gum and of upper teeth which are set in the upper gum and extend downwardly from the upper gum to teeth cusps. The oral cavity underlies the wall of the model of an upper dental arch.

The model of a lower dental arch contains a wall and a model of a lower gum and of lower teeth which are set in the lower gum and extend upwardly from the lower gum to teeth cusps. The oral cavity overlies the wall of the model of a lower dental arch.

The wall of one of the models of a dental arch comprises a surface which is opposite the model of the gum of the one of the models of a dental arch. The surface has an expanse which comprises a perimeter margin occluding the gum of the one of the models of a dental arch both to right and left of the medial plane.

Connection 20 comprises a sheet 33 of synthetic material having a flat upper zone 34 fastened to wall 26 posteriorly of its set of teeth by fasteners 36 and a flat lower zone 38 fastened to wall 28 posteriorly of its set of teeth by fasteners 40. Upper zone 34 and lower zone 38 join with opposite sides of a central zone 42 by upper and lower living hinge joints 44, 46 which provide for articulation of the arches by allowing sheet 33 to flex.

A cover 48 is separably attached to upper arch model 12 and covers the entirety of top surface 30 except for a small margin 49 of the continuous perimeter of top surface 30. Cover 48 has a continuous perimeter which substantially congruently registers with the continuous perimeter of top surface 30. Cover 48 has a uniform thickness between a top surface 52 and a bottom surface 54 except at the locations of posts 56 which extend from bottom surface 54 to make the distance from top surface 52 to the end of each post 56 greater.

In the particular typodont illustrated, the perimeters of top surface 30 and cover 48 are symmetrical about the median body plane 58 and each has seven sides. Posts 56 are arranged in a trapezoidal pattern which is symmetric about median plane 58 with two posts on each side of the median plane. Each post is set inwardly from the perimeter of cover 48 at the intersection of a respective pair of sides.

Top surface 30 has four blind holes 60 arranged in a trapezoidal pattern matching that of posts 56. Posts 56 fit within holes 60 to provide cover 48 with a friction or force fit to wall 26. The friction or force fit holds cover 48 on wall 26 over top surface 30 while allowing the cover to be separated from the wall by prying the cover off. For example, cover 48 may be separated manually by inserting one's fingernail between the perimeters of the cover and the wall and prying the cover away.

Figure 6:
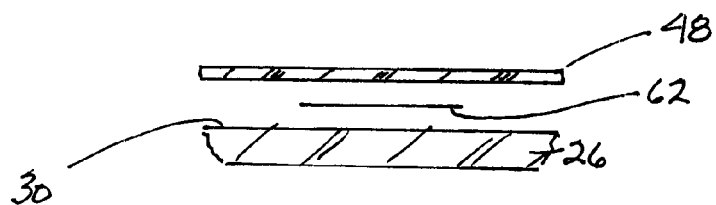
FIG. 6 is an exploded cross section view in the direction of arrows 6-6 in FIG. 7.
Figure 5:
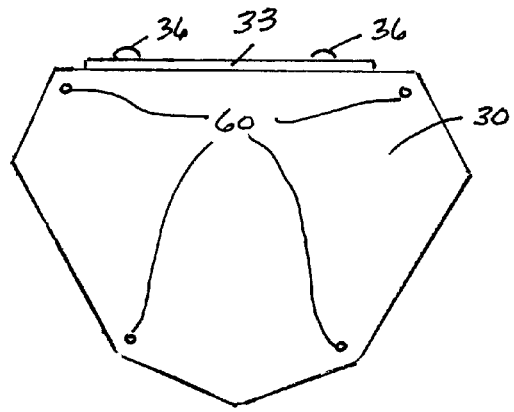
FIG. 5 is a view in the same direction as FIG. 2 but with a part having been removed.
Figure 7:
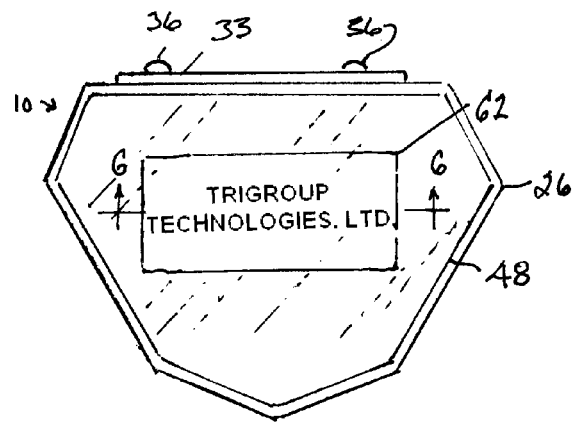
FIG. 7 is a view looking in the same direction as FIG. 2 but including an additional part.

Cover 48 is also transparent for allowing an element disposed between it and top surface 30 to be seen. FIGS. 6 and 7 show such an element as a flat sheet 62 containing indicia such as a company name, a product name, a design, or a logo. Sheet 62 is placed between top surface 30 and cover 48 as shown in FIG. 6 and the cover is attached to wall 26 by inserting posts 56 into holes 60, thereby trapping sheet 62 between cover 48 and wall 26. As shown by FIG. 7, the indicia on sheet 62 can be read or viewed through the transparent material of the cover.

Figure 8:
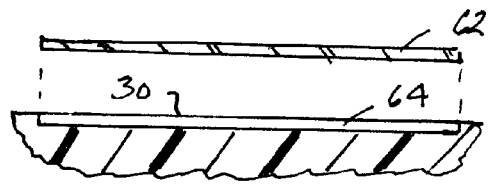
FIG. 8 is a view similar to FIG. 6, but showing another embodiment.

Sheet 62 can be properly located in any suitable manner on top surface 30 before cover 48 is attached to wall 26. FIG. 8 shows one possibility, a shallow recess 64 in top surface 30 having a shape for receiving and locating sheet 62. Alternatively a similar recess could be provided in the bottom of cover 48 instead and the sheet placed there. For example, sheet 62 can be a mylar sheet having a thickness of about 0.004 inch. A thicker sheet can be accommodated by increasing the depth of the cavity, or by two shallower cavities in confronting surfaces of the cover and the upper arch model. Instead of posts 56 being integral with cover 48 and holes 60 being in upper arch model 12, posts may be in the upper arch model and the holes in the cover.

Figure 9:
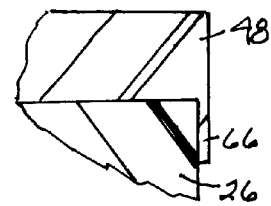
FIG. 9 is a view similar to FIG. 4, but showing still another embodiment.
Figure 10:
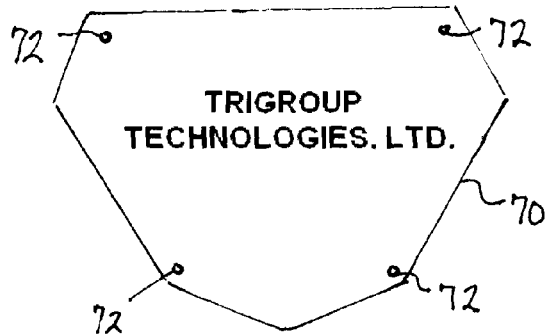
FIG. 10 is a top plan view of a different part which can used with the typodont of FIG. 1.
Figure 11:
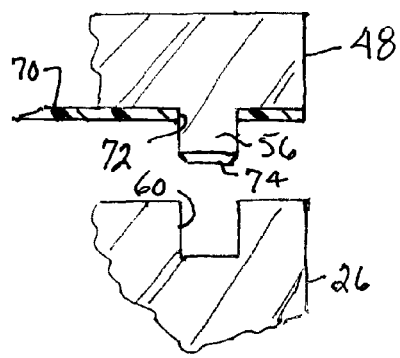
FIG. 11 is a fragmentary view similar to FIG. 4 showing use of the part of FIG. 10.

Instead of using posts and holes for separably attaching cover 48 to upper arch model 12, FIG. 9 shows a short narrow flange 66 extending around the perimeter of cover 48 and overlapping the side of wall 26. Cover 48 has a continuous perimeter which is still substantially congruent with the continuous perimeter of top surface 30 but now slightly overhangs the side of wall 26. Flange 66 is dimensioned to provide a friction fit against the side of wall 26. The flange may be continuous or discontinuous. FIG. 10 shows a flat sheet 70 intended to be placed between top surface 30 and cover 48. Sheet 70 has a shape essentially congruent with top surface 30 and cover 48. Sheet 70 contains four holes 72 located to allow the sheet to be properly aligned for congruity with both top surface 30 and cover 48 by aligning the holes 72 with posts 56 arranged in a matching pattern on cover 48 and inserting the posts into the holes as shown in FIG. 11. The posts can then be inserted into holes 60 in top surface 30 to create a final product having sheet 70 securely located and captured. FIG. 11 shows posts 56 to have tapered leads, or chamfers, 74 for facilitating their insertion into holes 60.

Figure 12:
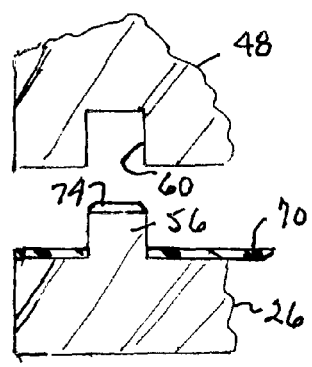
FIG. 12 is a fragmentary view showing a variation on FIG. 11.

FIG. 12 shows a reversal of the posts 56 and the holes 60 with the posts projecting from top surface 30 of wall 26 and the holes being in cover 48.

Figure 13:
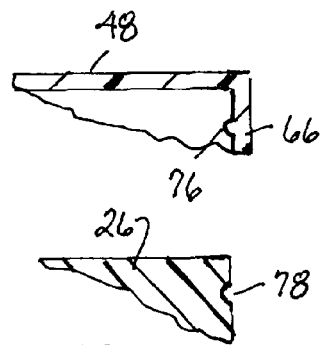
FIG. 13 is a cross section view similar to FIG. 9 showing another embodiment.

FIG. 13 shows flange 66 of cover 48 to have a locating feature 76 on its inner surface. An example of a locating feature is a bead 76 running along the flange parallel with sides of wall 26. When cover 48 is fully seated on wall 26, bead 76 lodges in a groove 78 in the sides of wall 26 which confronts flange 66. The material of the cover has slight flexibility which allows the flange to flex as the cover is being placed on wall 26 and bead 76 rides along the side of wall 26 and the flange to then relax upon the bead coming into registration with the groove. The bead and groove need not extend the full length of a side, and they need not be in all sides. They can be in just enough of the sides to provide a snap-on fit of the cover to the wall without making it too difficult to remove the cover. The flange can serve to locate a sheet like sheet 70 which has a perimeter exactly matching that of top surface 30 by placing the sheet inside the interior of the cover through the open bottom of the cover so that the sheet is bounded by the flange, and then placing the cover on the model.

Figure 14:
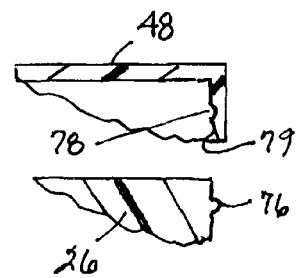
FIG. 14 is a view similar to FIG. 13 showing a variation.

FIG. 14 shows a variation where feature 76 is on the sides of wall 26 and groove 78 is in cover 48. The end of flange 66 has a taper 79 which upon riding across feature 76 will flex the flange slightly outward until groove 78 registers with bead 76 and the flange snaps into place with bead 76 lodging in groove 78.

In some dental arch models, the removable cover 30 need not be transparent. For example, the cover can be opaque and indicia may be present in any of one or more forms on the exterior of the cover. Such forms include labels, surface printing, hot stamping, and inscribing. In such models, when it is desired to display different indicia, the entire cover can be replaced with one that still fits to the arch model but has different indicia.

Figure 15:
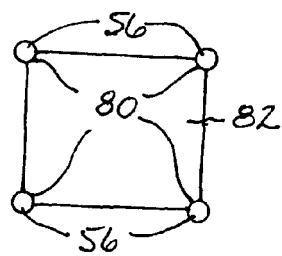
FIG. 15 is a plan view showing a portion of another embodiment.

FIG. 15 shows a rectangular sheet 82 like sheet 62 but having a scallop 80 at each corner with locates to a respective post 56. The posts can be in either wall 26 or cover 48 and fit to holes 60 in the other.

The embodiments which have been described so far use a friction- or a force-fit of the cover to the arch model or in the case of FIGS. 13 and 14 an interference fit. All of those types of fit avoid the use of adhesive. It is possible to use adhesive in an unobtrusive way by making holes 60 deep enough to receive a droplet of adhesive, such as an epoxy, which will make contact with a post 56 when the latter is inserted into the hole and upon setting hold the post in the hole while still allowing the cover to be removed. The cover lacks a flange and thereby allows the cover to be pried off by inserting an edge of a pry between the cover and wall 26. It can be re-attached by using a droplet of adhesive as described.

Another way to separably attach cover 48 to a dental arch model is by making through-holes in cover 48 such as in a pattern like that of holes 60 and then passing headed screws through the through-holes and tightening them in holes 60. The through-holes may have countersinks to allow the screw heads to be substantially flush with the outer surface of the cover when tightened. Polycarbonante is an example of a suitable material for cover 48.

What is claimed is:

1. A typodont comprising:
a model of an oral cavity containing a model of an upper dental arch and a model of a lower dental arch;
a connection for articulating the arches between closed and open conditions;
the model of an upper dental arch comprising a model of an upper gum disposed right and left of a medial plane of the oral cavity and of upper teeth which are set in the upper gum and extend downwardly from the upper gum to teeth cusps;
the model of a lower dental arch comprising a model of a lower gum disposed right and left of the medial plane and of lower teeth which are set in the lower gum and extend upwardly from the lower gum to teeth cusps;
one of the models of a dental arch comprising a wall, the gum of the one of the models of a dental arch being disposed between the wall and the teeth of the one of the models of a dental arch, the wall comprising a surface which is opposite the gum of the one of the models of a dental arch and which has an expanse which comprises a perimeter margin occluding the gum of the one of the models of a dental arch both to right and left of the medial plane;
a cover which overlies the surface and which is separably attached to the wall;
an element which is captured between the cover and the surface; and
the cover having a transparent zone for allowing at least a portion of the element to be viewed through the transparent zone, the element comprising a sheet which contains indicia for viewing through the transparent zone and which can be replaced by a different sheet when the cover is separated from the wall.

2. A typodont as set forth in claim 1 in which the surface comprises a continuous perimeter and the cover comprises a continuous perimeter which substantially congruently registers with the continuous perimeter of the surface.

3. A typodont as set forth in claim 1 in which one of the cover and the surface comprises multiple holes, and the other of the cover and the surface comprises multiple posts extending into the multiple holes via which the cover separably attaches to the wall.

4. A typodont as set forth in claim 1 in which the surface comprises a top surface and a side surface extending from a perimeter of the top surface, and the cover further comprises a flange which overlaps the side surface, and engages the side surface to separably attach the cover to the wall.

5. A typodont as set forth in claim 1 in which one of the cover and the surface comprises a locating feature for locating the element to the surface.

6. A typodont as set forth in claim 5 in which the locating feature comprises a cavity in one of the cover and the surface.

7. A method of making a model of a dental arch comprising:
fabricating a model of a dental arch comprising a wall, a model of a gum underlying the wall and disposed right and left of a medial plane of the model of a dental arch and of teeth which are set in the gum and extend downwardly from the model of a gum to teeth cusps, and the wall comprising a top surface opposite the teeth;
placing a sheet containing printed matter between the top surface of the wall and a transparent zone of a cover which is separably attachable to the wall; and separably attaching the cover to the wall to cover the sheet.

8. A model of a single dental arch comprising:
a wall presenting a top surface and a side surface extending downward from a perimeter of the top surface;
a model of an oral cavity underlying the wall and containing a model of a gum underlying the wall to the right and left of a medial plane of the oral cavity and of teeth which are set in the gum and extend downwardly from the gum to teeth cusps;
the top surface having an expanse which comprises a margin extending along the perimeter to occlude the gum both to the right and left of the medial plane; and
a cover which overlies the top surface and is separably attached to the wall, further including an element which is captured between the cover and the top surface, and the cover having a transparent zone for allowing at least a portion of the element to be viewed through the transparent zone, the element comprising a sheet which contains indicia for viewing through the transparent zone and which can be replaced by a different sheet when the cover is separated from the wall.

9. A model of a single dental arch as set forth in claim 8 including indicia disposed on an outer surface of the cover.

10. A model of a single dental arch as set forth in claim 8 in which the cover comprises a perimeter which substantially congruently registers with the perimeter of the top surface.

11. A model of a single dental arch as set forth in claim 8 in which one of the cover and the top surface comprises multiple holes, and the other of the cover and the top surface comprises multiple posts extending into the multiple holes via which the cover separably attaches to the wall.

12. A model of a single dental arch as set forth in claim 8 in which at least one of the top surface and the cover comprises a locating feature for locating the sheet to the top surface.

13. A model of a single dental arch as set forth in claim 8 in which the cover and the wall separably attach via holes in one of the top surface and the cover and posts in the other of the top surface and the cover, the posts extending into the multiple holes.

14. A model of a single dental arch as set forth in claim 8 in which the cover comprises a continuous perimeter which substantially congruently registers with the perimeter of the top surface of the wall.

15. A model of a single dental arch as set forth in claim 14 in which the cover further comprises a flange which overlaps the side surface of the wall, and engages the side surface of the wall to separably attach the cover to the wall.

16. A model of a single dental arch as set forth in claim 15 in which one of the flange and the side surface of the wall comprises a bead and the other of the flange and the side surface of the wall comprises a groove which receives the bead to separably attach the cover to the wall.

\* \* \* \* \*